United States Patent [19]

Poveromo

[11] Patent Number: 5,222,891
[45] Date of Patent: Jun. 29, 1993

[54] ONE-PIECE CAST RESIN DENTAL DOWEL WITH VISIBLE HORIZONTAL INDEX

[76] Inventor: Melvin D. Poveromo, 1160 Kane Concourse, Bay Harbor Islands, Miami Beach, Fla. 33154

[21] Appl. No.: 809,336

[22] Filed: Dec. 18, 1991

[51] Int. Cl.⁵ .............................................. A61C 19/00
[52] U.S. Cl. ...................................................... 433/74
[58] Field of Search ............................................ 433/74

[56] References Cited

U.S. PATENT DOCUMENTS

| 2,851,728 | 9/1958 | Spalten et al. | 433/74 |
| 3,413,725 | 12/1968 | Stern et al. | 433/74 |
| 3,454,256 | 7/1969 | Stern et al. | 433/74 |
| 3,470,614 | 10/1969 | Kelly | 433/74 |
| 3,521,354 | 7/1970 | Stern et al. | 433/74 |
| 3,896,548 | 7/1979 | Zahn | 433/74 |
| 4,056,585 | 11/1977 | Waltke | 433/74 |
| 4,139,943 | 2/1979 | Dragan | 433/74 |
| 4,363,625 | 12/1982 | der Avanessian | 433/74 |
| 4,371,340 | 2/1983 | Imaizumi | 433/74 |
| 4,457,709 | 7/1984 | Moore | 433/74 |
| 4,721,464 | 1/1988 | Roden et al. | 433/74 |
| 4,840,565 | 6/1989 | Poveromo | 433/74 |
| 4,997,370 | 3/1991 | Mayclin | 433/74 |

Primary Examiner—John J. Wilson
Attorney, Agent, or Firm—Sughrue, Mion, Zinn, Macpeak & Seas

[57] ABSTRACT

A one-piece molded dental dowel-pin adapted to be fixed to a tooth die and having an integral elongated locking-and-indexing arm which, after final trimming of a dental model, has an outer tip which is visible to a human observer when the tooth die is inserted in the trimmed, final dental model.

14 Claims, 3 Drawing Sheets

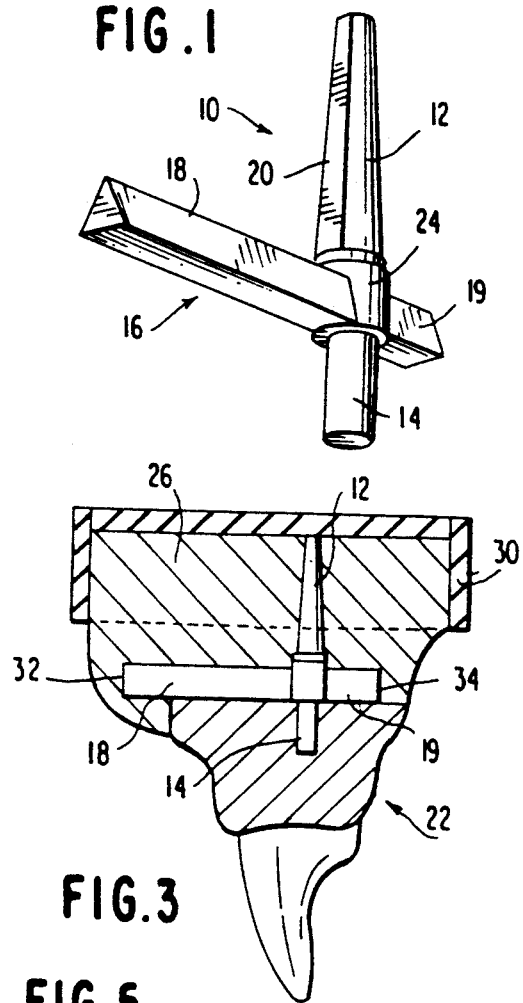
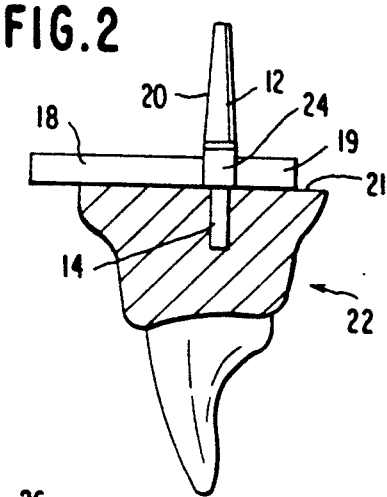
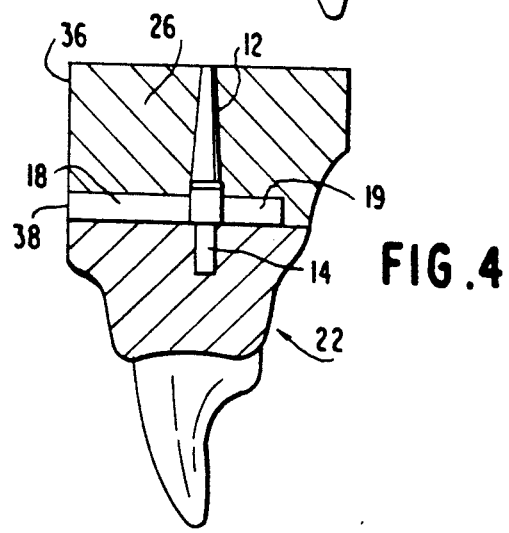
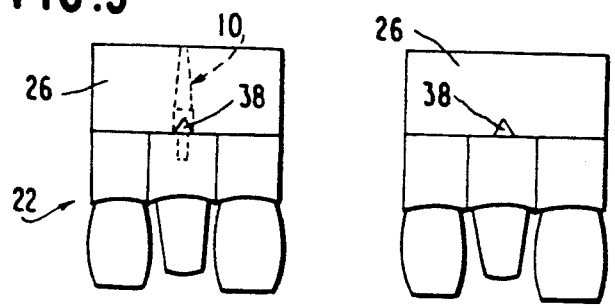
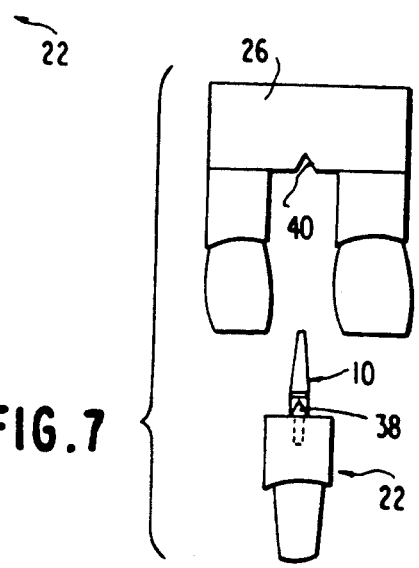
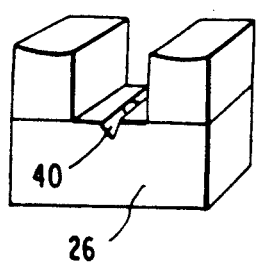

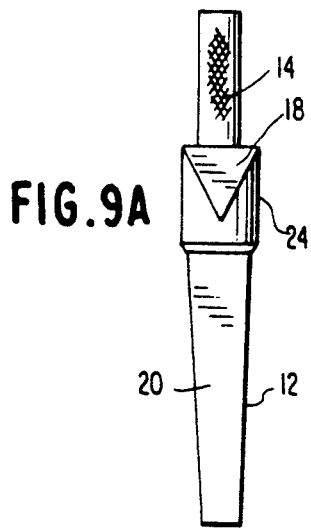
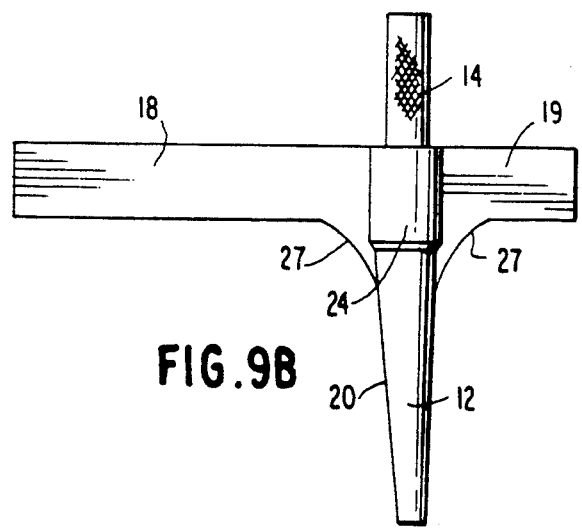
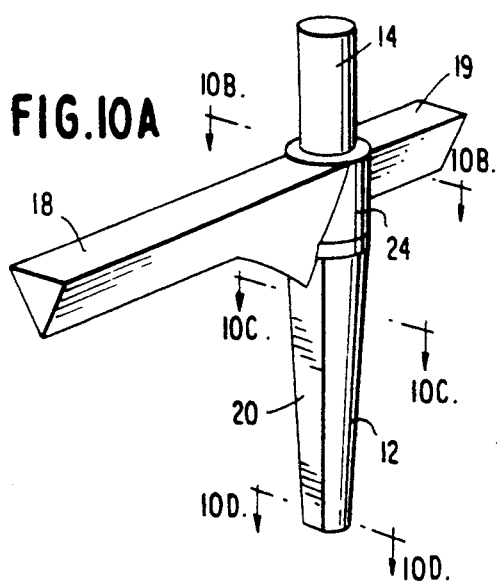
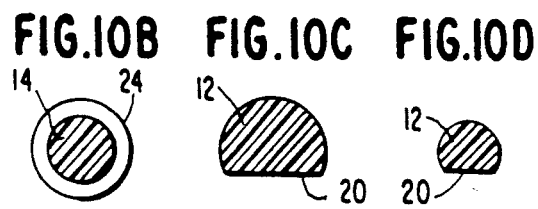
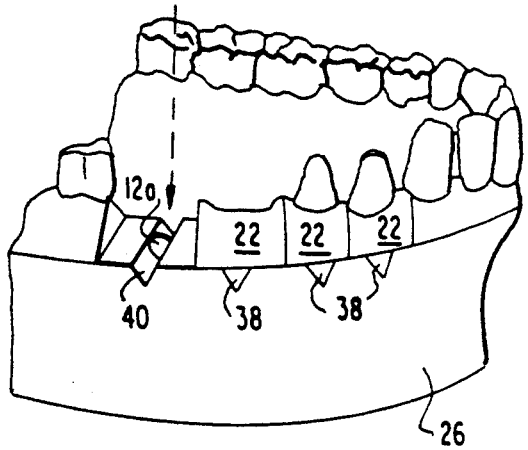

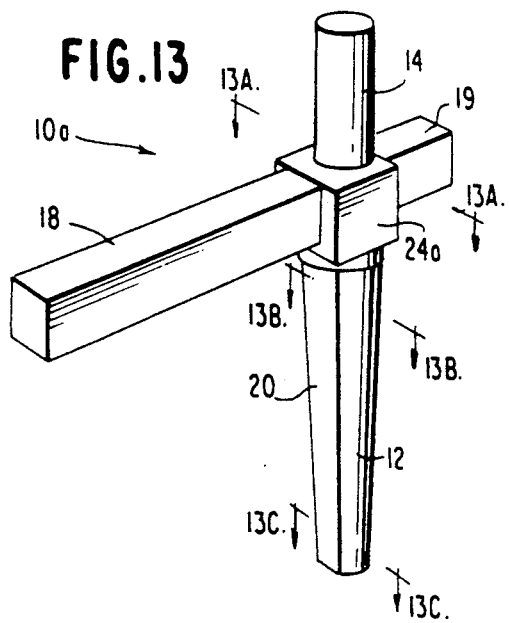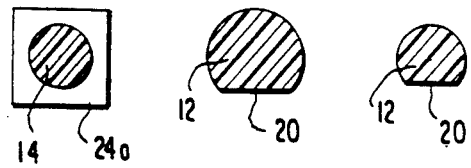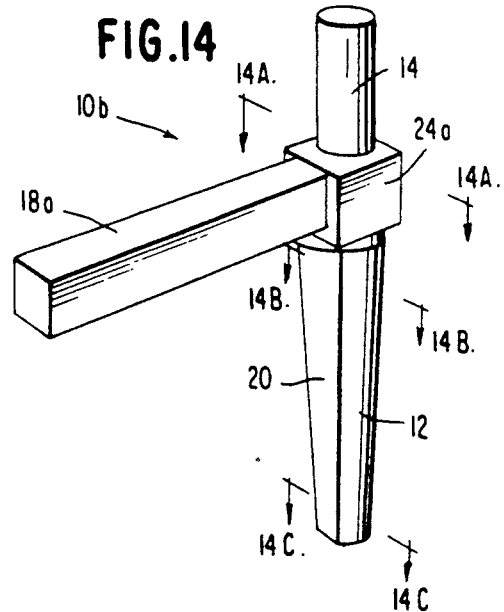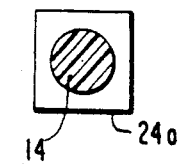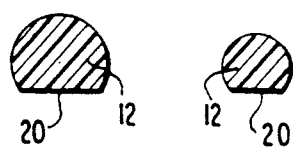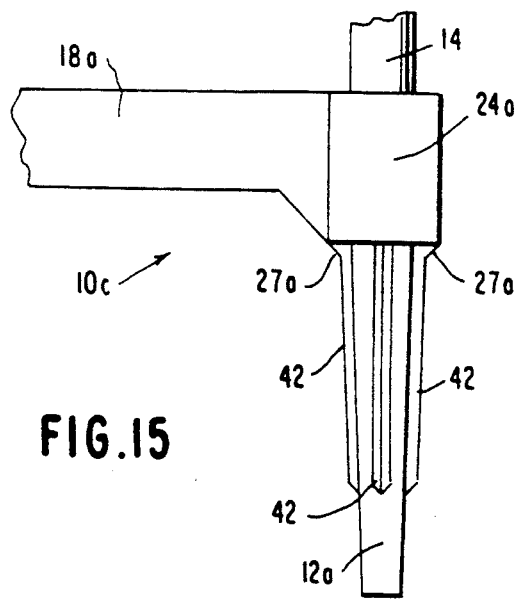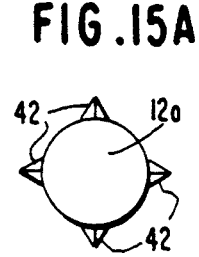

ONE-PIECE CAST RESIN DENTAL DOWEL WITH VISIBLE HORIZONTAL INDEX

FIELD OF THE INVENTION

My invention relates generally to the field of dental models and, more particularly, to a novel dowel-pin for a tooth die, and to a method of making a dental model incorporating such a dowel-pin.

The present invention is an improvement of my prior invention described and claimed in my prior U.S. Pat. No. 4,840,565, issued Jun. 20, 1989, and entitled, "Tooth-Die Dowel-Pin and Locking Assembly and Method of Making a Dental Model Incorporating Said Assembly". This patent is expressly incorporated herein by reference for its background information.

In order to fabricate a crown or inlay on a tooth, an impression of a patient's mouth is taken, and a reproduction is made in the dental laboratory. Since the reproduction is a solid positive model of the mouth, it is necessary to isolate reproductions or dies of the individual teeth which have been prepared to receive a restoration. This isolation is accomplished by various types of dowel pins, each of which is secured to a respective die by either a first known process wherein a dowel-pin is inserted into the impression material before the dental model is fabricated, or a second known process wherein the entire solid dental model is first made and, then, holes are drilled above the individual prepared tooth areas or dies to receive individual dowel pins which are inserted and glued into the drilled holes.

In the fabrication of dental models and individual tooth dies, it is extremely important to have both an accurate reproduction of each tooth die and also of the relationship between each individual die and the adjacent model teeth. Since the natural teeth that are positioned in the dental arch are stationary, each individual die on the dental model must be accurately positioned with respect to the entire model so as to correspond to the natural teeth. If there is any movement of the die in the model, then the fabrication of a dental restoration (crown, inlay, etc.) will not be accurate, because, then, the model will not be an accurate reproduction of the natural teeth.

Furthermore, when individual crowns are to be fabricated to restore two or more natural teeth and are to be intentionally joined (soldered) on the model, any movement of the die or dies will cause the final restoration to be inaccurate since the movement of the dies creates an inaccurate reproduction of the natural teeth. Similarly, when crowns are fabricated on dies, and removable appliances are fabricated to be inserted on or into these crowns, any movement of the dies would produce an inaccurate restoration for obvious reasons.

The prior art is replete with various types of dowel pins for incorporation into each individual die. For example, there are (a) single vertical dowel pins with tapers, (b) double vertical pins and (c) single and double vertical pins with corresponding sleeves that are embedded into the stone model. In each case, the intention is to isolate each individual die, and the purpose of the single or double vertical pins is to prevent movement of the die on the master model. Since each die, with its inserted dowel-pin, rests upon the base of the dental model, and since this base has a flat surface, the only security of the die is the vertical dowel that penetrates into the base. As a result, a fulcrum or pivoting effect commonly occurs since there is nothing to prevent the vertically extending conventional dowel-pin from moving. As a result of this fulcrum effect, the die can move in five directions: bucally; lingually; mesially; distally; and also upwardly since there is also nothing available to prevent upward movement of the dowel-pin. Furthermore, often the die bottom that rests upon the flat base surface of the dental model is rough, broken or contains debris that prevents the die from properly seating on the surface of the model base. As a result, and in addition to the fulcrum effect of such a vertical dowel-pin, there is produced an inaccuracy in the relationship of the die to the model and, consequently, an inaccuracy in the fabrication of any restoration which is to be installed on the natural teeth. In addition, since dental models are not standard, and since tooth lengths are not standard, it is often necessary to have an extremely long die. Furthermore, dental models may be of different thicknesses. As a result, it should be clear that, as the length of the die increases, or as the thickness of the dental model increases, the so-called fulcrum effect of the die and dowel-pin also increases. Since there is no standard length of die or model, the conventional dowel-pin or pins do not prevent movement of the relative to the model.

There are many U.S. patents relating to means for positioning the dowel-pin when making a dental model according to the first process cited above, i.e., a process wherein the dowel-pin is positioned within a negative impression which is then filled with dental material or plaster which surrounds and embeds the dowel-pin, as opposed to the second process (with which my invention is associated) wherein the entire negative impression is filled with dental material or plaster to produce a positive master casting or model into which holes are selectively drilled for receiving subsequently inserted dowel-pins.

U.S. Pat. No. 2,851,728 shows a dental dowel-pin having a single hole therein for receiving an elongated, rod-like repositioning gauge supported in the base stone of a dental model; thus, there is no provision for preventing the above-mentioned fulcrum effect. Furthermore, the single rod-like gauge passes through more than one dowel-pin, a construction which has limited practical value compared to an individual locking device for each dowel pin.

U.S. Pat. Nos. 3,413,725; 3,454,256; and 3,521,354 merely disclose dowel-positioning systems, and also show the use of channel forming members located on the end of a dowel-pin to form a channel in the base stone for facilitating the removal of a selected tooth die from the stone.

U.S. Pat. No. 4,457,709 shows a coiled wire rod for holding a dowel-pin in position in a dental cavity of a tooth impression during the pouring of dental die casting material into the cavity.

U.S. Pat. No. 3,896,548 shows a dental model provided with horizontal wedges which are inserted in mating sockets spanning the parting lines between adjacent tooth dies for maintaining alignment of the tooth dies within the model.

U.S. Pat. Nos. 4,056,585 and 4,139,943 show dowel-pin constructions for use in a dental die.

U.S. Pat. No. 4,997,370 describes a two-piece metal dowel-pin which prevents rotation of a tooth die but having an index which is invisible after the model has been trimmed. This patent is also expressly incorporated herein by reference for its background information.

SUMMARY OF THE INVENTION

Therefore, the object of my invention is to provide an improved dowel-pin which is one-piece, which is molded or cast from plastic, and which has a horizontal locking index which is visible after the model to which the tooth-die has been inserted is trimmed.

BRIEF DESCRIPTION OF THE DRAWING

FIG. 1 is a perspective view of a first embodiment of my one-piece cast resin dental dowel-pin having an horizontal index in accordance with my invention;

FIG. 2 is a cross-sectional view showing the novel dowel-pin inserted in a tooth-die before the glue has hardened;

FIG. 3 is a cross-sectional view, similar to the of FIG. 2, showing the tooth die after the glue has hardened and after the second half of the model has been poured;

FIG. 4 is a cross-sectional view, similar to that of FIG. 2, showing the novel dowel-pin and its horizontal index, after the model has been trimmed;

FIG. 5 is a front view of the final model showing the triangular shape of the horizontal index and showing the inserted dowel-pin in dashed lines;

FIG. 6 is a front view, similar to that of FIG. 5, but showing only the horizontal triangular index which is actually visible or exposed after trimming of the die;

FIG. 7 is a front view showing the model and the tooth-die in which the novel dowel-pin is inserted, after the tooth-die has been removed from the model;

FIG. 8 is a perspective upside-down view of the model after the tooth-die has been removed, and showing the complementary triangular recess which was formed in the model for receiving the horizontal index of the novel dowel-pin;

FIGS. 9A and 9B are front and side views, respectively, of the novel dowel-pin;

FIG. 10A is an enlarged perspective view, in an upside-down position, of the first embodiment of my invention;

FIG. 10B is a cross-sectional view showing the cylindrical configuration of the fastening end of the dowel-pin;

FIG. 10C and 10D are cross-sectional views showing that the free end-portion of the dowel-pin is tapered and has one flat side;

FIG. 11 is a perspective view of a finished dental model containing a plurality of tooth-dies locked in place with my novel dowel-pin having a horizontal index which is visible to an observer;

FIG. 12 is similar to FIG. 11, except that there has been removed from the dental model one of the tooth dies in which my novel dowel-pin has been fixed, and shows the corresponding V-shaped complementary groove or recess in the corresponding vacant location of the model;

FIG. 13 is a perspective view of another embodiment of my novel dowel-pin;

FIGS. 13A, 13B and 13C are cross-sectional views of three different portions of the embodiment of FIG. 13;

FIG. 14 is a perspective view of a third embodiment of the invention, which embodiment is similar to that of FIG. 13 but which has a horizontal index projecting from only one side of the dowel-pin;

FIGS. 14A, 14B and 14C are cross-sectional views of three different portions of the embodiment of FIG. 14;

FIG. 15 is a side view of a fourth embodiment of the invention; and

FIG. 15A is a bottom view of FIG. 15.

DESCRIPTION OF PREFERRED EMBODIMENTS

FIG. 1 illustrates a first embodiment of my novel one-piece resin cast dowel-pin which is cast or molded as a rigid single piece from an engineering thermoplastic resin such as a polycarbonate resin. The basic integral components of the novel dowel pin comprise a tapered free end-portion 12, a knurled fastening end-portion 14 which is longitudinally aligned with the tapered end-portion 12, and a transverse index 16 which has a long index-segment 18 extending in one direction from the junction of the end-portions 12 and 14, and which has a shorter index-segment 19 extending in the opposite direction from this junction. In use, the end-portions 12 and 14 have a vertical orientation, and the index 16 has a horizontal orientation.

As shown more clearly in FIGS. 10A, 10B, 10C and 10D, the tapered free end-portion 12 has at least one flat surface 20 which prevents rotation of the dowel pin 10 (and of the tooth die 22 fixed thereto) within the dental model 26 as shown, for example, in FIG. 3 and FIG. 4; the tapered free end-portion 12 can have up to four flat surfaces. The knurled fastening-end portion 14 has a cylindrical shape with a circular cross-section as shown more clearly in FIGS. 10A and 10B. My novel dowel-pin is cast or molded so that in this embodiment it has a reinforcing cylindrical collar 24 formed at the junction or intersection of free end-portion 12, fastening end-portion 14, the long index segment 18 and the short index segment 19. For improved strength and rotation prevention, fillets 27 are formed at one or both of the connection points of collar 24 with the index segments 18 and/or 19. These fillets 27 merge with respective ones of the index segments 18 and 19, extend longitudinally along the free end portion 12, and project transversely outwardly in opposite directions. The conventional taper of the free end portion 12 allows the dowel-pin 10 to be removed from the dental model 26.

With reference to FIG. 2, glue is placed on the fastening-end portion 14 for cementation in a bore hole which was formed in the tooth die 22 during the first pour of dental stone-mix in a two-pour process, and, at the same time, a small amount of glue is also placed under the index-segments 18 and 19 at their interface with the upper surface 21 of the tooth die 22.

As shown in FIG. 3, after the glue has hardened, the second half of the dental model 26 is poured, using a second pour of a stone-mix with the usual rubber mold 30; the second pour forms a rough base model 26 that extends beyond the outer tips 32 and 34 of the long and short index-segments 18 and 19, respectively.

As clearly shown in FIG. 4, when the resulting rough model 26 is "trimmed" at one side 36, for example, the trimmed outer end or tip 38 of the long index-segment 18 is now flush with the trimmed side 36 and is visible or exposed to human observation in the trimmed final model. This visible triangular outer end 38 is also shown in the front views of FIGS. 5 and 6. FIGS. 7 and 8 are front and perspective views, respectively, showing the tooth die 22 (with my novel dowel-pin affixed thereto) removed from the final dental model 26 and showing therein the corresponding V-shaped groove or recess 40 which was formed during the second pour of the stone-mix and which receives the horizontal index 16 with its triangular long and short index-segments 18 and 19 for locking the dowel-pin against rotation in the model. FIG. 8 shows the dental model in an upside-down position.

Thus, it is clear that my novel dowel-pin construction has at least two major advantages over prior art constructions: (1) the interlocking of the triangular horizontal index 16 with the correspondingly-shaped recess or groove 40 provides a highly stable construction which prevents rotation of the tooth die within the dental model; and (2) the exposed tip 38 of the horizontal index-segment 18 provides a tooth die "seat" which is visible to a dentist or dental technician, whereas in the prior art there was no standard method of observing the seat of the tooth die in a dental model made by the two-pour process.

Because of the selected length of the long horizontal index-segment 18, even after model trimming there will always be the visible index tip 38 to permit a person to ascertain the exact "seat" of the tooth die; in prior art dowel pins with a horizontal index, the index is buried within the final dental model and is not visible, thereby not enabling a human observer visually to ascertain the exact seat of the tooth die.

FIGS. 9A and 9B are front and side views, respectively, of this first embodiment of my invention. Typically, index segments 18 and 19 are sixteen and six mm long, respectively, and have a height of approximately 3.0 mm. The free end portion 12 is approximately 12.5 mm long.

FIG. 11 illustrates a dental model 26 showing inserted therein a plurality of tooth dies 22 containing my novel dowel-pin, and also shows the visible horizontal index tips 38.

FIG. 12 is similar to FIG. 11 but shows one of the tooth dies removed from the dental model, thereby exposing the corresponding locking groove or recess 40 containing a bore hole 12a for receiving the removably insertable tapered free end 12 of the dowel-pin 10.

FIGS. 13, 13A, 13B and 13C are similar to FIGS. 10A, 10B, 10C and 10D and show a second embodiment of the invention wherein the collar 24a is square or rectangular (rather than circular).

FIGS. 14, 14A, 14B and 14C show a third embodiment of the invention wherein the dowel-pin 10b has only a longer horizontal index-segment 18a; that is, there is no shorter horizontal index-segment 19 as found in the first and second embodiments of the invention.

FIGS. 15 and 15A show a fourth embodiment which is like the previous embodiments but in which the dowel-pin 10c has a tapered free end-portion 12a having a circular cross-section. Projecting outwardly from the surface of the end-portion 12a are from one to four longitudinally extending ribs 42 which, like the flat surface(s) 20 of the previous embodiments, lock the dowel pin against rotation when inserted in the dental model. The ribs 42 are connected by fillets 27a index-segment 18a and collar 24a. In a modification of this embodiment, the free end-portion 12a has various combinations of ribs 42 and flat surface(s) 20, such as one flat surface 20 and three ribs 42. The ribs are inherently formed during the process of molding the novel dowel pin and, as illustrated in FIG. 15, one of the ribs 42 merges, via fillet 27a, with the index segment 18a.

Even though I have described and illustrated only several embodiments of my invention, it is to be understood that obvious variations of these embodiments are encompassed by my invention the scope of which is limited only by the appended claims.

What is claimed is:

1. A one-piece molded non-metallic plastic dental dowel-pin in combination with a tooth die for use in a finally trimmed dental model that was made by a two-pour process, said combination comprising
   a tooth die made by a first pour and having an outer periphery and an upper surface, and for use with
   a base model made by a second pour and having a groove therein, said dowel-pin being adapted to be fixed to said tooth die and to be removably inserted in a bore in said base model; said dowel-pin comprising:
   a fastening end-portion extending in a first direction and adapted to be fixed said tooth die;
   an elongated free end-portion extending in a direction opposite to said first direction and adapted to be removably inserted in said base model; and
   an integral elongated locking-and-indexing arm portion having a first index-segment extending from a junction of said fastening and free end-portions in a transverse direction relative to said first and opposite directions; said arm portion matching and being adapted to be received in said groove in said base model when said free end-portion is inserted in said base model; said first index-segment having a length which is sufficiently long to extend along said upper surface and outwardly beyond said outer periphery of said tooth die so that, after the dental model has been finally trimmed, an outer tip of said first index-segment is visible in an outer surface of said base model.

2. A one-piece molded dental dowel-pin as defined in claim 1, wherein said arm portion has a second index-segment which extends in a direction opposite to that in which said first index-segment extends, and which, after the dental model has been finally trimmed, is buried inside the dental model and is invisible on the outer surface of the dental model.

3. A one-piece molded dental dowel-pin as defined in claims 1 or 2, further comprising a collar at the junction of said fastening and free end-portions.

4. A one-piece molded dental dowel-pin as defined in claim 3, wherein said collar is cylindrical.

5. A one-piece molded dental dowel-pin as defined in claim 3, wherein said collar is rectangular.

6. A one-piece molded dental dowel-pin as defined in claim 3, wherein said arm portion is joined to said collar and to said free end portion by at least one fillet which merges with said arm portion, which extends longitudinally along said free end portion, and which projects outwardly from said free end portion in said transverse direction.

7. The one-piece molded dental dowel-pin as defined in claim 2, wherein said second index-segment is shorter than said first index-segment.

8. A one-piece molded dental dowel-pin as defined in claim 1, wherein said elongated free end-portion has at least one longitudinally extending integral rib projecting substantially transversely outwardly from a surface of said elongated free end-portion.

9. A one-piece molded dental dowel-pin as defined in claim 8, wherein said elongated free end-portion has a circular transverse cross-section, and wherein there are four longitudinally extending integral ribs equally spaced about a circumference of said elongated free end-portion.

10. A one-piece molded dental dowel-pin as defined in claim 8, wherein said elongated free end-portion has at least two longitudinally extending integral ribs projecting substantially transversely outwardly in opposite directions from a surface of said elongated free end-portion.

11. A one-piece molded dental dowel-pin as defined in claims 1, wherein said elongated free end-portion is tapered in a direction away from said junction, and has at least one flat surface.

12. A one-piece molded dental dowel-pin as defined in claim 11, wherein there is only one said flat surface, and wherein there are three longitudinally extending integral ribs projecting substantially transversely outwardly from a surface of said elongated free end-portion.

13. A one-piece molded dental dowel-pin as defined in claim 1, wherein said arm portion has a triangular cross-section adapted to fit in a complementarily configured groove in a top surface of said base model, said top surface being in a plane which is approximately perpendicular to said bore and to said outer surface of said base model.

14. A two-pour process for making a dental model using a one-piece molded dental dowel-pin without any parting plate and having a fastening end-portion extending in a first direction and fixed to a tooth die, a free end-portion extending in a direction opposite to said first direction and adapted to be removably inserted in a dental model, and an integral elongated locking-and-indexing arm extending from a junction of said fastening and free end-portions in a direction transverse to said first and opposite directions and being adapted to be received in a corresponding groove in the dental model when the free end-portion is inserted in the dental model, the elongated arm having a length which is sufficiently long so that, after the dental model has been finally trimmed, an outer tip of the elongated arm is visible on an outer surface of the dental model; said process comprising the steps of:

fixing the fastening-end portion of the dowel-pin in a bore hole of the tooth die so the free end-portion and the integral elongated arm of the dowel-pin are exposed on a base surface of the tooth die;

pouring a dental stone-mix over the assembled dowel-pin and tooth die so that the elongated arm is completely embedded within the stone-mix;

allowing the stone-mix to dry and harden to form a rough dental model; and trimming the rough dental model, in at least a portion thereof in which the elongated arm is embedded, to form a trimmed outer surface at which an outer tip of the elongated arm is visible and is flush with said outer surface.

* * * * *